United States Patent
Harvey et al.

(10) Patent No.: US 6,200,819 B1
(45) Date of Patent: *Mar. 13, 2001

(54) METHOD AND APPARATUS FOR PROVIDING DILUENT GAS TO EXHAUST EMISSION ANALYZER

(75) Inventors: R. Neal Harvey, Santa Ana; Allen F. Dageforde, Orange, both of CA (US)

(73) Assignee: Horiba Instruments, Inc., Irvine, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/606,242

(22) Filed: Feb. 23, 1996

Related U.S. Application Data

(63) Continuation-in-part of application No. 08/536,401, filed on Sep. 29, 1995, now Pat. No. 5,756,360.

(51) Int. Cl.⁷ ...................................................... G01N 1/14
(52) U.S. Cl. ............................ 436/179; 73/1 G; 73/23.31; 73/863.03; 73/863.83; 422/83; 422/94; 436/134; 436/181
(58) Field of Search ........................ 422/94, 83; 436/134, 436/177, 179, 181; 73/23.31, 1 G, 31.02, 31.03, 869.02, 863.03, 863.11, 863.83, 864.34, 864.81, 863.61

(56) References Cited

U.S. PATENT DOCUMENTS

| | | |
|---|---|---|
| 2,755,663 | 7/1956 | Smith et al. . |
| 3,469,442 | 9/1969 | Brueckner . |
| 3,593,023 | 7/1971 | Dodson et al. ...................... 73/23.31 |
| 3,741,009 | 6/1973 | Bordeaux . |
| 3,750,472 | 8/1973 | Ducousset . |
| 3,924,445 | 12/1975 | Konomi et al. . |
| 3,965,749 | 6/1976 | Hadden et al. ...................... 73/23.31 |
| 3,975,953 | 8/1976 | Smith et al. . |
| 4,344,107 | 8/1982 | Webber et al. . |
| 4,586,367 * | 5/1986 | Lewis . |
| 4,637,366 | 1/1987 | Cowles . |
| 4,706,492 | 11/1987 | Jones, Jr. et al. . |
| 4,823,591 * | 4/1989 | Lewis . |
| 5,756,360 * | 5/1998 | Harvey et al. ....................... 436/179 |

* cited by examiner

*Primary Examiner*—Jan Ludlow
(74) *Attorney, Agent, or Firm*—Brooks & Kushman PC

(57) ABSTRACT

An apparatus adapted for analyzing exhaust emissions by using a small fraction of a continuously-extracted exhaust sample combined with a pollutant-free diluent through a system of critical flow orifices at a predetermined and precisely controlled flow ratio. A small quantity of gas is extracted from the diluted exhaust gas available which is diluted with the contaminant-free air or nitrogen to produce a mixture having a dew point below ambient air temperature and satisfying the flow requirements of the analysis system. The diluted sample may then be analyzed to obtain the total mass of pollutants through identification of the instantaneous exhaust concentration rate and the exhaust mass flow rate or through identification of the concentration of pollutants collected in a sample bag and the total exhaust volume.

16 Claims, 3 Drawing Sheets

US 6,200,819 B1

METHOD AND APPARATUS FOR PROVIDING DILUENT GAS TO EXHAUST EMISSION ANALYZER

CROSS REFERENCE TO RELATED APPLICATION

This application is a continuation-in-part of U.S. Ser. No. 08/536,401 filed Sep. 29, 1995 now U.S. Pat. No. 5,756,360.

BACKGROUND OF THE INVENTION

This invention relates to a gas sampling device to measure the concentration of exhaust substances (i.e., emissions of, for example, CO, $CO_2$, hydrocarbons HC, $NO_x$, $SO_x$ and the like) contained in the exhaust gas of an automotive vehicle.

A conventional method of measuring the mass of components in exhaust gases uses the CVS (Constant Volume Sampling) method. The CVS method continuously dilutes all of the exhaust gases from an engine with ambient air to a constant and known volume flow rate. The constant flow rate is controlled by drawing the diluted exhaust gases through a volumetric measuring device such as a critical flow venturi or a positive displacement pump. By continuously collecting a small fraction of the total diluted flow in a bag during a test cycle, the mass of a component can be determined by measuring the concentration of the component in the bag at the end of a test and multiplying by the total diluted volumetric flow measured during the test. The CVS method works well as long as the concentration of the component measured is large compared to the concentration of that component in the dilution air. As progress is being made in the reduction of the mass of pollutants emitted from an engine, the contribution made to the measurement by the diluent is no longer negligible. In fact, sometimes the concentration of a pollutant in the diluent air is larger than the concentration in the exhaust gas. An obvious solution to this situation is to use a purified diluent instead of ambient air. For the CVS technique, this is an expensive and impractical approach because of the large volumes of diluent required. Typically the minimum volume of diluent required is eight to ten times the maximum instantaneous exhaust gas flow rate. This large quantity of diluent is necessary in order to reduce the dew point of the gas mixture to below ambient temperature, thereby preventing condensation of the moisture present in the exhaust gas.

An alternate technique to measure mass emissions and avoid measuring the pollutants in the dilution air is to measure the exhaust concentrations before CVS dilution and separately determine the exhaust mass flow. Additional flow measurements must be made to utilize this method.

To determine the instantaneous mass flow of an exhaust component using the CVS method, the following technique can be used. The instantaneous exhaust gas flow rate can be calculated by measuring the diluent flow rate into the CVS with a flow measurement device such as a smooth approach orifice and mathematically subtracting this from the CVS flow rate. By using the instantaneous exhaust flow rate and the undiluted exhaust concentrations the instantaneous mass emissions of any component may be determined.

In order to measure the concentration of exhaust gas components directly, analysis must either be done at elevated temperatures in specially designed instrumentation or the water which condenses when the exhaust gas is cooled must be removed before analysis. Both of these approaches have disadvantages. Instruments designed to operate at elevated temperatures are expensive and usually require considerable care and maintenance. Analysis on a "wet basis" is desirable to eliminate the errors introduced by removing the water from the sample. When the water vapor in the gas is condensed and removed, some of the pollutants are removed with the water. The concentrations indicated when analyzing a sample on a "dry basis" are higher than "wet basis" analysis due to the decrease in volume caused by removal of the water. The "wet basis" analysis can only be approximated from the "dry basis" analysis. The residual errors are undesirable.

SUMMARY OF THE INVENTION

According to the present invention, a small quantity of undiluted exhaust gas is extracted and diluted with contaminant-free air or nitrogen producing a mixture having a dew point below ambient temperature and satisfying the flow requirements of the analysis system. Analysis is performed at ambient temperature without water extraction or loss of any exhaust emissions components. The undiluted concentrations are readily obtained by multiplying the diluted sample concentrations by the dilution ratio.

This invention is adapted to be used for analyzing exhaust emissions by using a small fraction of a continuously-extracted exhaust sample combined with a pollutant-free diluent through a system of critical flow orifices at a predetermined and precisely controlled flow ratio. The apparatus and method of the present invention includes the general steps of: (1) Determining the working dilution ratio; (2) introducing calibration gases to establish the operating-dilution ratio; (3) extracting an aliquot of high dew point exhaust gas; (4) diluting the exhaust gas sample with a dry, pollutant-free diluent; (5) maintaining the exhaust gas at a temperature above the dew point of water through dilution; and (6) delivering the diluted exhaust gas to the analysis system at a sufficient flow rate to satisfy the flow requirements of the gas analysis system. Once delivered to the analyzer, the diluted gas can then be analyzed and the undiluted pollutant concentrations obtained by multiplying by the dilution ratio. In practice, the dilution ratio is determined by analyzing the undiluted calibration gas and dividing that concentration by the concentration of the diluted calibration gas produced by the diluter as determined by the analyzer system.

According to the present invention, sample and diluent flow orifices have throat sizes that are properly sized to accurately establish the dilution ratio of diluent gas to exhaust gas. The inlet pressure to the diluent orifice is controlled to a pressure equal to the sample orifice inlet pressure by a pneumatic relay. The sample and diluent orifices exit into a common reduced pressure manifold. The manifold pressure is maintained at a reduced pressure sufficient to create critical flow through both orifices. By situating the orifices and related fluid lines within an oven, the temperature of the undiluted sample is maintained above the dew point of exhaust gas, thus eliminating condensation problems. This oven arrangement also maintains the orifices at equal temperatures, thus circumventing dilution ratio variations.

The sample and diluent orifices are preferably of the critical flow variety, however (or alternately) critical flow venturis, subsonic orifices, or subsonic venturis may be substituted for the critical flow orifices. The invention maintains constant dilution ratio with subsonic orifices and subsonic venturis by maintaining equal pressure at the inlets and equal, reduced pressure at the outlets of the sample and dilution orifices or venturis.

The diluted gas produced by any embodiment of the diluter of the present invention may then be analyzed to obtain the total mass of pollutants. Analysis according to the present invention may be accomplished in one of two ways. First, the diluted sample may be continuously analyzed as it is produced by the diluter system through first measuring the instantaneous exhaust concentration then multiplying this quantity by the corresponding exhaust mass flow rate. This will produce a figure corresponding to the instantaneous mass flow rate of the pollutant. By integrating the instantaneous mass flow rate over time, the total mass of pollutants produced during a test cycle can then be obtained.

Second, the diluted sample may be collected in one or more sample bags by metering a small amount of the diluted exhaust at a flow rate proportional to the exhaust flow rate using a mass flow controller. The mass flow controller meters the gas passing therethrough in response to an operator's instructions delivered through a control signal. The total mass of pollutants may then be obtained by analyzing the sample bag and multiplying the concentration of pollutants by the dilution ratio and the total exhaust volume.

DETAILED DESCRIPTION OF THE PREFERRED EMBODIMENT

Figure 1:
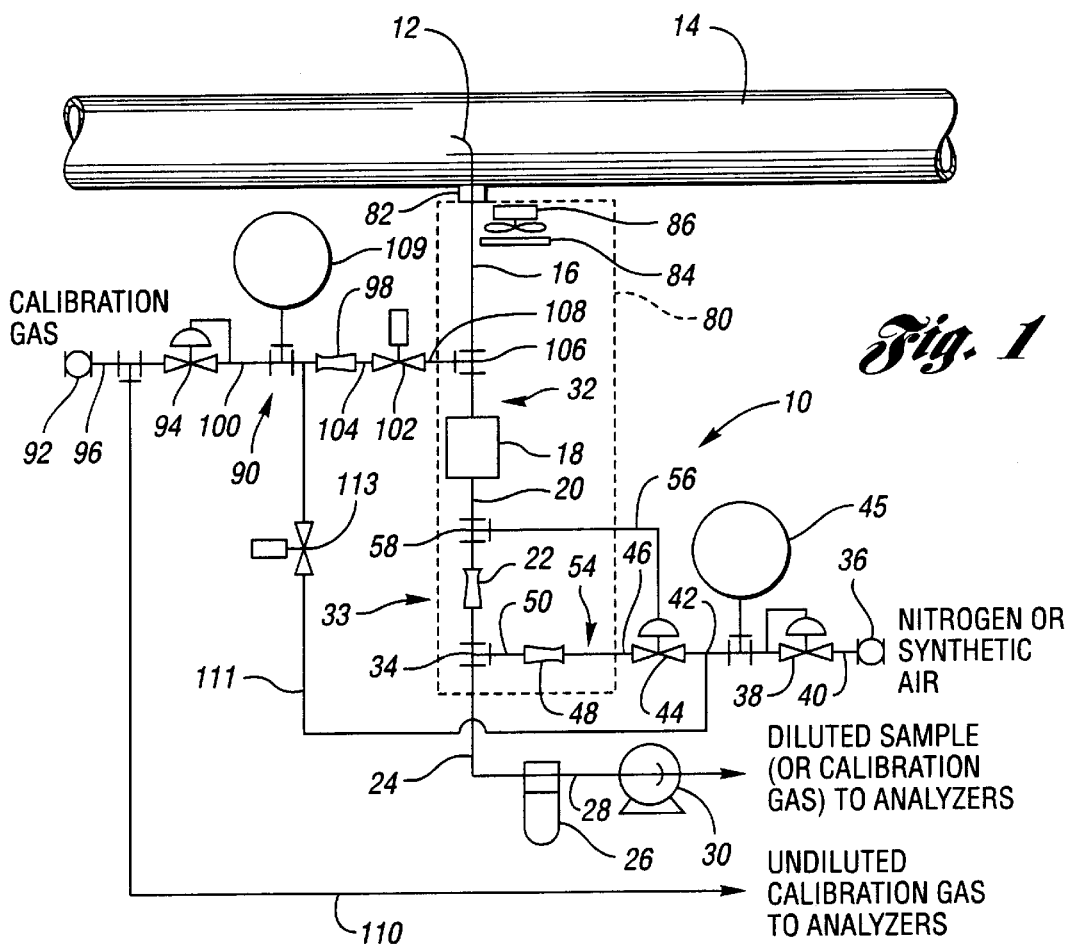
FIG. 1 is a diagrammatic illustration of a system for providing diluted gas to an exhaust emission analyzer constructed in accordance with a preferred embodiment of the present invention.

Referring now to FIG. 1, a diagrammatic representation of a pneumatically-operated apparatus for providing diluted exhaust gas to an exhaust emission analyzer is depicted and is identified generally by the reference numeral 10. The apparatus 10 comprises a tail pipe adapter 12 for coupling to an internal combustion engine exhaust pipe 14. Exhaust from the exhaust pipe 14 is introduced through an exhaust sample inlet line 16. The sample inlet line 16 terminates at a prefilter 18. The inlet line 16 as well as all of the other fluid lines of the present invention are preferably composed of stainless steel for corrosion resistance. The prefilter 18 is provided to eliminate particulates from the exhaust sample, the presence of which would otherwise build up on the critical flow surfaces of the apparatus 10. The prefilter 18 is of any type known in the art that is capable of removing particulates.

The exhaust sample exits the prefilter 18 into a prefilter outlet line 20 which forms a connector between the prefilter 18 and, according to the preferred embodiment of the apparatus illustrated in FIG. 1, a sample critical flow orifice or critical flow venturi 22. As is known, the venturi includes a convergent cone and a divergent cone with a throat therebetween. At the outlet side of the sample orifice 22 is a first bulkstream line 24 which fluidly connects the sample orifice 22 with a pulsation dampener 26. The dampener 26 is located in the sample path downstream of the sample orifice 22 but upstream of the sample analyzer (not shown). A second bulkstream line 28 connects the dampener 26 to a vacuum pump 30. The dampener 26 dampens or smoothes pulsations produced by the pump 30.

The exhaust sample inlet line 16, the prefilter 18, the prefilter outlet line 20, and the sample orifice 22 define a sample fluid path, generally illustrated as 32. The first bulkstream line 24, the pulsation dampener 26, and the second bulkstream line 28 define a bulkstream path generally illustrated as 33.

A quantity of pollutant-free diluent gas (such as nitrogen or air) is introduced into the sample path 32 at a fluid junction 34, which is a point that is downstream of the sample orifice 22. A source of gas, generally illustrated as 36, provides the diluent necessary for proper operation of the apparatus 10.

A key feature of the present invention is the ability to control the dilution ratio by utilizing a pressure relay or regulator on the diluent. An emission analyzer typically requires between four to ten cubic feet per hour to operate. Because the typical emissions analysis system may comprise seven or eight analyzers, the total flow rate requirements may reach 45 to 50 cubic feet per hour. For gasoline-fueled engines, the optimum dilution ratio is approximately 8:1, this being defined as eight parts diluent to one part exhaust gas.

The diluent gas is delivered to a pressure regulator 38 via a first diluent connecting line 40. The diluent pressure regulator 38 reduces the nitrogen or air from the source of gas 36 to a working level of pressure. A second diluent connecting line 42 connects the diluent pressure regulator 38 to a diluent pneumatic relay 44. A pressure gauge 45 is provided on the line 42 to indicate diluent supply pressure. A third diluent connecting line 46 is fitted between the diluent pneumatic relay 44 to a diluent critical flow orifice or critical flow venturi 48. A fourth diluent connecting line 50 fluidly connects the diluent orifice 48 to the first bulkstream line 24 at the fluid junction 34. The first, second, third and fourth diluent connecting lines 40, 42, 46 and 50, respectively, combined with the pressure regulator 38 and the diluent pneumatic relay 44, respectively, the pressure gauge 45 and the diluent orifice or venturi 48 define a diluent path, generally illustrated as 54. A pressure reference line 56 connects the diluent pneumatic relay 44 with the prefilter outlet line 20 at a fluid junction 58 at a point that is upstream of the sample orifice 22. The diluent pneumatic relay 44 senses the pressure at the inlet of the sample orifice 22 through line 56 and controls the pressure at the inlet side of the diluent orifice 48 such that it is equal to the sample pressure entering the sample orifice 22.

Figure 2:
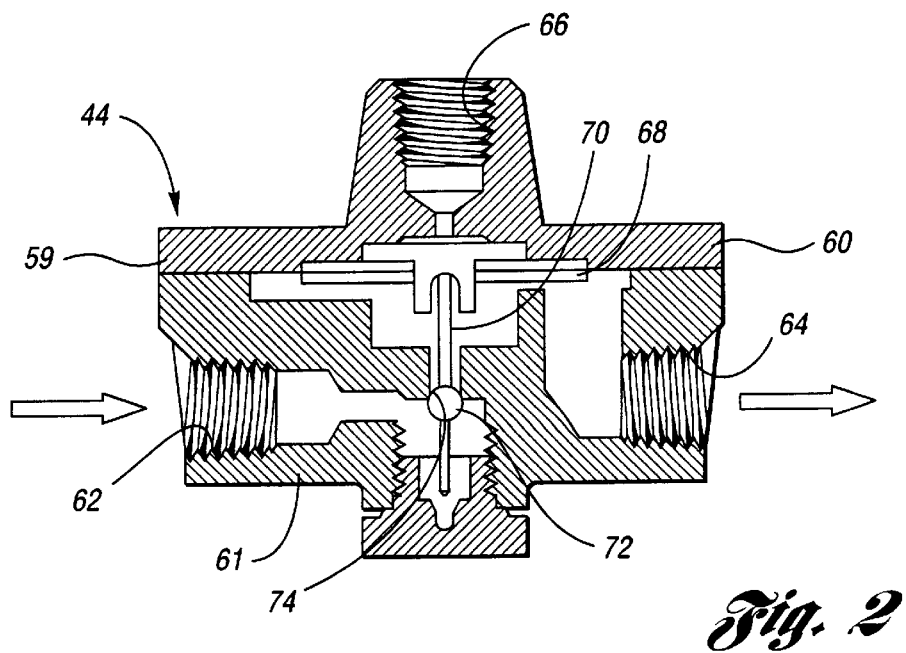
FIG. 2 is a sectional view of a preferred pneumatic relay of the present invention.

The diluent pneumatic relay 44, illustrated in sectional view in FIG. 2, is a modified version of a known pressure regulator, such as Model 63SD Flow Controller sold by Moore Products. This relay is critical in that it controls the diluent pressure at the inlet to the dilution orifice 48 so that it is at the same pressure as the exhaust sample. The relay 44 includes a body 59 having an upper body half 60 and a lower body half 61. The lower body half 61 has a diluent gas inlet 62 and a diluent gas outlet 64 formed therein. A diaphragm 68 includes a downward-depending stem 70 having a valve member 72. The member 72 is selectively movable off of a seat 74, and, when so moved, allows gas to pass between the inlet 62 and the outlet 64. The pressure of the gas entering the reference inlet 66 controls movement of the diaphragm 68 and, consequently, flow of the diluent gas through the relay 44. (The above-mentioned Model 63SD has been modified by the removal of a spring from between the diaphragm 68 and the inner wall of the upper half of the body 60.)

The pump 30 provides appropriate vacuum to establish the flow of the sample gas through the sample path 32, the diluent path 54, and the bulkstream path 33. The throats of the sample and diluent orifices 22 and 48, respectively, are sized in order to properly control the flows of the exhaust gas and the diluent gas. Preferably, the throat diameter of these orifices range from 0.1 mm to 1.5 mm. Generally, the inlet and outlet pressures to and from the orifices 22 and 48 are controlled to force gas to flow at a sonic velocity (the critical flow). The flow-through of the orifices 22 and 48 is determined according to the following formula:

$$\text{Critical flow-through} = \frac{C \times P}{\sqrt{T}}$$

Where:
C is a constant of proportionality;
P is the absolute pressure at the inlet of the orifice; and
T is the absolute temperature at the inlet.
So long as the absolute pressures at the inlet and outlet of the critical flow orifices 22 and 48 satisfy the relationship defined by $$\frac{P_1}{P_2} < \left(\frac{2}{K+1}\right)^{\frac{k}{k-1}}$$

critical flow (sonic velocity) is present through the orifices. $P_2$ is the absolute pressure at the outlet from a given orifice; $P_1$ is the absolute pressure at the inlet to a given orifice; and K is the ratio of the specific heat at constant pressure to the specific heat at constant volume for the gases flowing through the orifices (K is termed "adiabatic exponent"). See John K. Vennard, *Elementary Fluid Mechanics*, John Wiley and Sons, Inc., 1961, pages 9, 10, 157.

According to the preferred embodiment, the inlet pressure to the diluent orifice 48 is controlled to a pressure equal to the pressure at the inlet of the sample orifice 22. The pressure at the inlet of the orifice 22 may typically range between —1 p.s.i.g. and 4 p.s.i.g. Because the sample and diluent orifices 22 and 48, respectively, exit into the common bulkstream path 33, equal pressure drops are produced across the two orifices 22 and 48, even during transient sample pressure events. Accordingly, at all times the flow rates through the two orifices 22 and 48 are at a constant ratio, preferably in the range of approximately 8 parts diluent to 1 part exhaust sample.

To assist in assuring constant volume ratios and to circumvent dilution ratio variations, the orifices 22 and 48 are maintained at a constant elevated temperature (typically between 160–180 degrees F.), thus eliminating the possibility that the orifices 22 and 48 operate at different temperatures. An oven 80, illustrated by broken lines, is provided for this purpose. The oven 80 includes an extension sleeve 82 and further includes a source of heat 84 (such as a heating coil) and an air bath stirrer 86 (such as a fan) for evenly circulating the warm air within the interior of the oven 80.

In addition to maintaining the orifices 22 and 48 at substantially equal elevated temperatures, the provision of the oven 80 also assures that the temperature of the exhaust gas sample is maintained at a level which is above the dew point of exhaust gas. In engine exhaust, water is present in the exhaust as a combustion product of fuel. The water vapor in the exhaust would ordinarily condense if the exhaust gas were simply cooled to ambient air temperature before analysis, an undesirable condition in that the condensed water interferes with the analysis and, in addition, would undesirably remove some of the pollutants (such as $NO_2$) before analysis. The present system of maintaining the sample at a temperature above the dew point until after dilution (the sample and diluent gases are combined at the junction 34 which is situated within the oven 80) coupled with using a dry diluent gas avoids this problem. Dilution of the sample exhaust gas reduces the dew point to below ambient temperature. Once dilution is completed, the bulkstream gas exits the oven 80 and is allowed to cool to ambient temperature prior to analysis.

To determine the working dilution ratio (the ratio of sample flow rate plus diluent flow rate divided by sample flow rate) established by the orifices 22 and 48, a calibration system, indicated generally as 90, is provided. The system 90 includes a calibration gas source 92, a pressure regulator 94 connected to the gas source 92 by a first line 96, a critical flow orifice 98 connected to the pressure regulator 94 by a second line 100, and a solenoid valve 102 connected with the critical flow orifice 98 by a third line 104. The solenoid valve 102 is connected to the sample inlet line 16 at a junction 106 by a fourth calibration line 108 at a point upstream from the prefilter 18. A pressure indicator 109 is fitted to the second line 100. A direct line 110 is provided between the source 92 and the analyzer (not shown). A fluid line 111 connects the second line 100 of the calibration system 90 to second diluent connecting line 42 of the diluent path 54. A two-way solenoid valve 113 is fitted to the line 111 to provide the ability to flow either diluent gas or undiluted calibration gas through both orifices at normal operating flow rates. This is useful for accurate determination of the dilution ratio.

By opening the solenoid valve 102 and with an excess flow rate of calibrating gas (in excess of what the apparatus 10 actually draws from the exhaust pipe 14), the calibrating gas flows into the sample orifice 22 and excess calibrating gas "overflows" through the sample inlet line 16 and into the exhaust pipe 14. This floods the inlet side of the sample orifice 22 with calibration gas and assures that a 100% concentration of calibrating gas is passing through the orifice 22. Thereafter, the calibrating gas concentration is diluted by the set ratio created by the two orifices 22 and 48. The diluted calibrating gas can then be analyzed. By allowing a quantity of undiluted calibrating gas to flow directly from the source 92 through the calibration line 110 to the analyzer for analysis, the undiluted concentration is determined. The ratio of these two concentrations establishes the operating-dilution ratio of the system.

Figure 3:
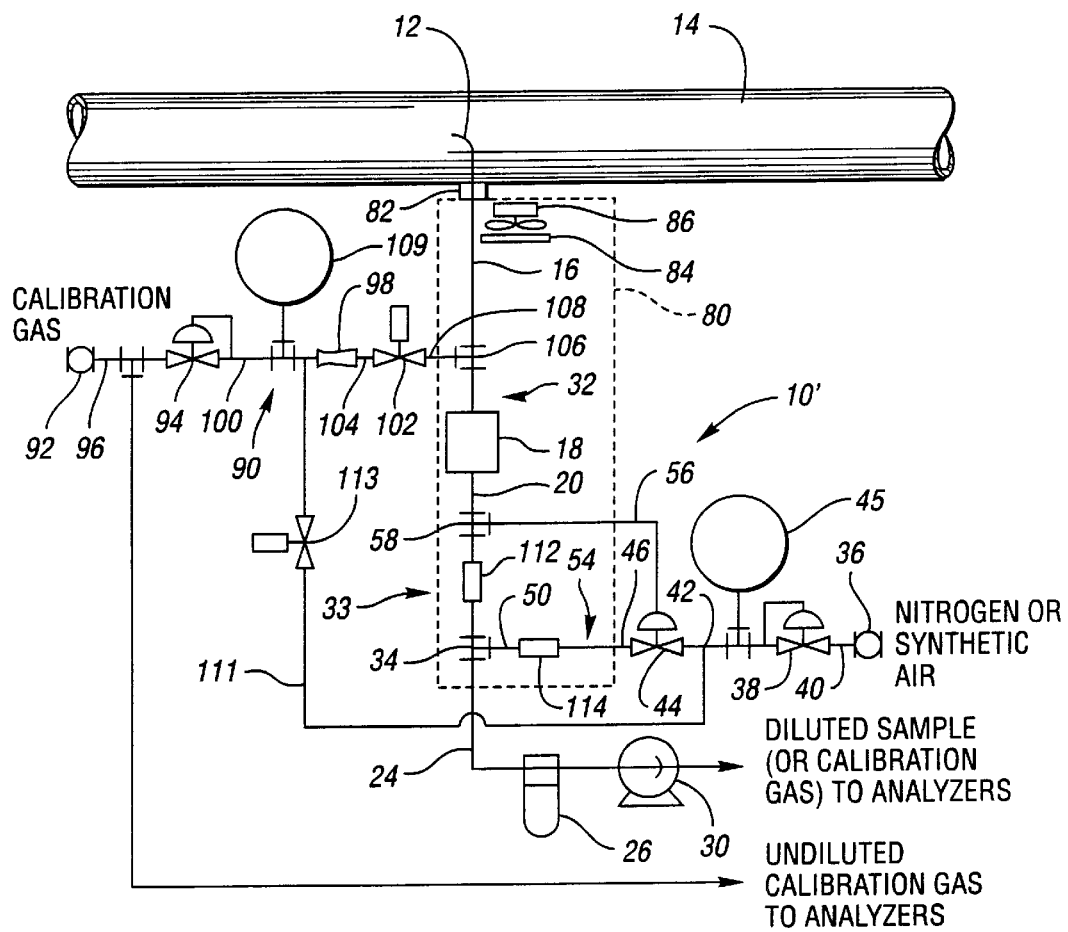
FIG. 3 is a diagrammatic illustration of a system for providing diluent gas similar to the system of FIG. 1 constructed in accordance with an alternate embodiment of the present invention.

An alternate embodiment of the present invention is set forth in FIG. 3, where an apparatus for providing diluent gas to an exhaust emission analyzer is depicted and is identified generally by the reference number 10'. The apparatus 10'is substantially identical to the apparatus 10 shown in FIG. 1 and described in relation thereto, but includes a sample flow control valve 112 in lieu of the sample orifice 22 of FIG. 1 and a diluent flow control valve 114 in lieu of the diluent critical flow orifice 48. The flow control valve may be adjusted manually or electronically. Calibration and operation of the apparatus 10' is substantially identical with that of the apparatus 10.

Figure 4:
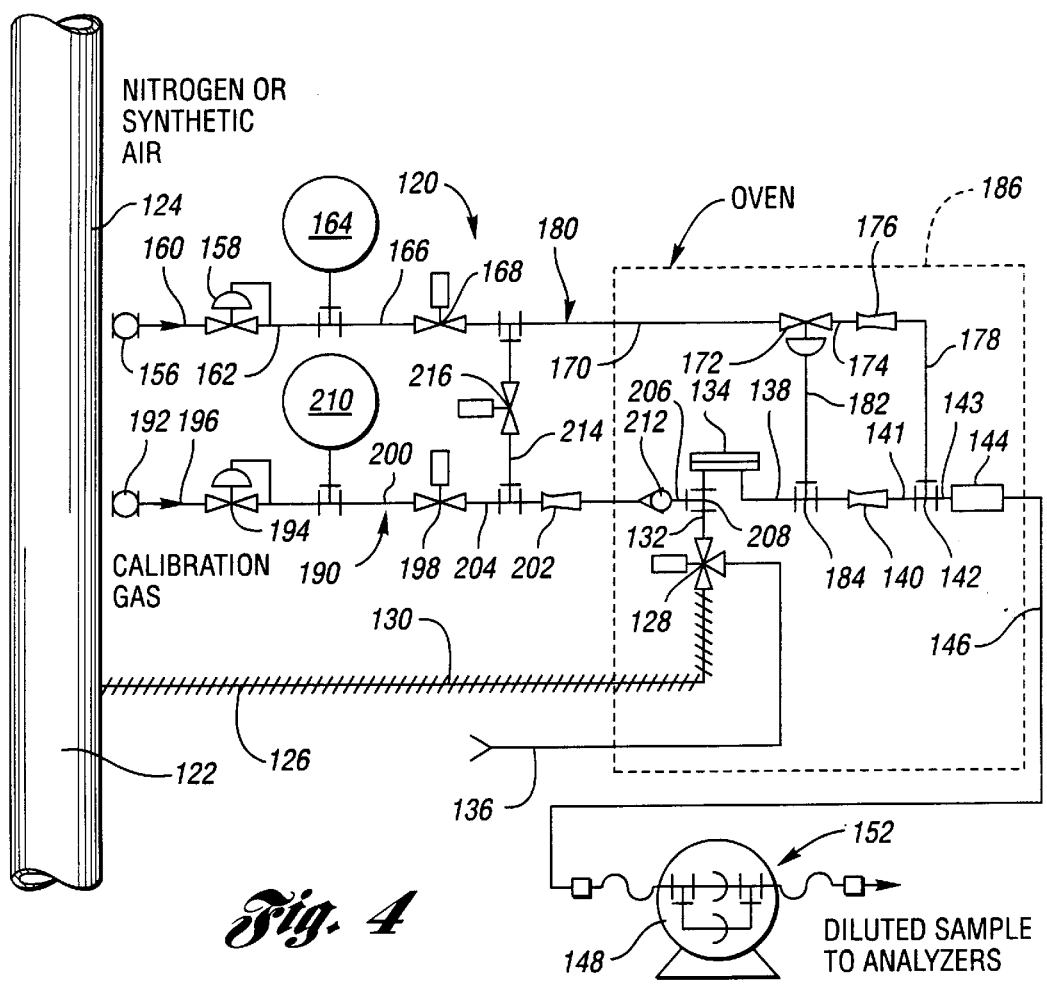
FIG. 4 is a diagrammatic illustration of a system for providing diluted gas to an exhaust emission analyzer constructed in accordance with an additional alternate embodiment of the present invention.

Referring now to FIG. 4, a diagrammatic representation of an additional alternate embodiment of a pneumatically-operated apparatus for providing diluted exhaust gas to an emission analyzer is depicted and is identified generally by the reference numeral 120. The apparatus 120 comprises a tail pipe adapter 122 for coupling to the internal combustion engine exhaust pipe 124. Exhaust from the exhaust pipe 124 is introduced through an exhaust sample inlet line 126. The sample inlet line 126 terminates at a three-way solenoid valve 128. The inlet line 126 as well as all of the other fluid lines of the present invention are preferably composed of stainless steel or other suitable materials such as Teflon® for the sake of corrosion resistance. The line 126 is provided with a heating element such as a sleeve 130 to maintain the sample gas at an elevated temperature (typically 160–180 degrees F.) to prevent water condensation. A connecting line 132 connects the three-way solenoid valve 128 to a prefilter 134. The prefilter 134 is provided to eliminate particulates from the exhaust sample, the presence of which would otherwise build up on the critical flow surfaces of the apparatus 10. The prefilter 134 is of any type known in the art that is capable of removing particulates.

An ambient air line 136 is open to ambient air as illustrated. The air line 136 provides a path for the flow of gases prior to taking a sample from the heated line. The line 136 draws in ambient air. As illustrated, the valve element of the three-way valve 128 that is connected to the air line 136 is normally open.

The exhaust sample exits the prefilter 134 into a prefilter outlet line 138 which forms a connection between the prefilter 134 and a sample critical flow orifice or critical flow venturi 140. At the outlet side of the sample orifice 140 is a first bulkstream line 141 which fluidly connects the sample orifice 140 with a fluid junction 142. A second bulkstream line 143 fluidly connects the fluid junction 142 with a buffer tank 144. The buffer tank 144 is located in the sample path downstream of the sample orifices 140 and 176 but upstream of a pump 148 (not shown in FIG. 4). A third bulkstream line 146 connects the buffer tank 144 to a pump 148. The buffer tank 144 dampens or smoothes pulsations produced by the pump 148.

The exhaust sample line 126, the prefilter 134, the prefilter outlet line 138, and the sample orifice 140 defines a sample fluid path, generally illustrated as 150. The first bulkstream line 142, the buffer tank 144, and the second bulkstream line 146 define a bulkstream path generally illustrated as 152.

According to the embodiment of FIG. 4, a quantity of pollutant-free diluent gas (such as nitrogen or air) is introduced into the sample path 150 at a fluid junction 154, which is a point that is downstream of the orifice 140. A source of gas, generally illustrated as 156, provides the diluent necessary for proper operation of the apparatus 10.

The diluent gas is delivered to a pressure regulator 158 via a first diluent connecting line 160. The diluent pressure regulator 158 reduces the nitrogen or air from the source of the gas 156 to a working level of pressure, typically between 10 psi and 20 psi. A second diluent connecting line 162 connects the diluent pressure regulator 158 to a pressure gauge 164 which is provided on the line 162 to indicate diluent supply pressure. A third diluent connecting line 166 connects the pressure gauge 164 to a two-way solenoid valve 168. As illustrated, the input side of the valve 168 (connected to the line 166) is normally in a closed position.

A fourth diluent connecting line 170 connects the valve 168 to a diluent pneumatic relay 172. The relay 172 and its function are the same as the relay 44 set forth in FIGS. 1 and 2 and discussed in relation thereto. A fifth diluent connecting line 174 connects the relay 172 to a diluent critical flow orifice or critical flow venturi 176. A sixth diluent connecting line 178 fluidly connects the orifice 176 to the first bulkstream line 142 at the fluid junction 154. The first, second, third, fourth, fifth, and sixth diluent connecting lines 160, 162, 166, 170, 174, and 178, respectively, combined with the pressure regulator 158, the pressure gauge 164, the solenoid valve 168, the relay 172, and the orifice 176 define a diluent path, generally illustrated as 180. A pressure reference line 182 is connected to the prefilter outlet line 138 at a fluid junction 104, a point upstream of the sample orifice 140. The diluent pneumatic relay 172 senses the pressure at the inlet of the sample orifice 176 through the line 182 and controls the pressure at the inlet side of the diluent orifice 176 such that it is equal to the sample pressure entering the sample orifice 140.

As with the heated line 126, the orifices 140 and 176 are maintained at a constant elevated temperature (typically between 160–180 degrees F.) to eliminate the possibility that the orifices 140 and 176 operate at different temperatures. An oven 186, illustrated by broken lines, is provided for this purpose. As with the oven 60 shown in FIGS. 1 and 3 above, both a heating source and a circulating fan (neither shown) are provided in operable association with the oven 186.

To determine the working dilution ratio established by the orifices 140 and 176, a calibration system, indicated generally as 190, is provided. The system 190 includes a calibration gas source 192, a pressure regulator 194 connected to the gas source 192 by a first line 196, a two-way solenoid valve 198 connected to the regulator 194 by a second line 200, a constant flow orifice 202 connected to the valve 198 by a third line 204, and a fourth line 206 connecting the orifice 202 to the line 132 at a junction 208. A calibration gas pressure gauge 210 is fitted to the second line 200. A one-way check valve 212 is fitted to the fourth line 206. As with the calibration system 90 of FIG. 1, the system 190 of FIG. 4 allows the operator to introduce a calibration gas into the sample inlet to establish the working dilution ratio provided by the orifices employed in the invention, or alternatively to calibrate the analyzers (not shown) to indicate the calibration gas concentration. (As noted, the working dilution ratio is the ratio of calibration gas concentration divided by the diluted concentration.)

Like the line 111 of the embodiments of FIGS. 1 and 3, a fluid line 214 of the diluent path 180 connects the fourth diluent line 170 to the third line 204 of the calibration system 190. A two-way solenoid valve 216 is fitted to the line 214 to provide the ability to flow either diluent gas or undiluted calibration gas through both orifices at normal operating flow rates. This is useful for accurate determination of the dilution ratio.

Operation of the apparatus 120 of FIG. 4 is substantially similar to the steps taken with respect to the apparatus 10 of FIG. 1 and the apparatus 10' of FIG. 3. Regardless of the embodiment of the mini-diluter of the present invention, a diluted sample is produced through operation of the apparatus. While the various embodiments of the apparatus (10, 10' and 120) are useful in preparing a sample that is not contaminated by ambient air pollutants (through the use of pure nitrogen or pure air), an additional step directed to the determination of the total mass of pollutants is needed in order to calculate the total mass of exhaust emissions.

Figure 5:
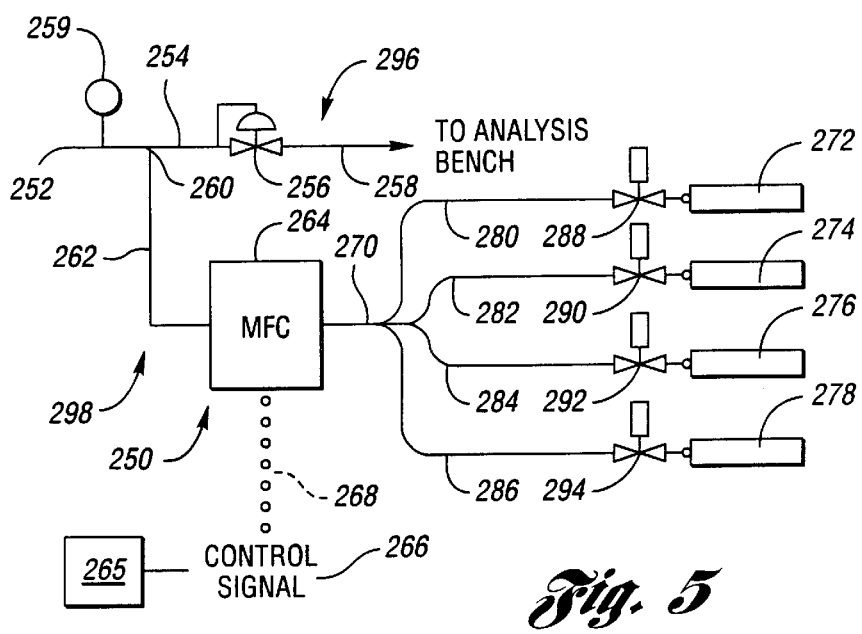
FIG. 5 is a diagrammatic illustration of a system for analyzing the diluted sample produced according to the system of FIGS. 1, 3, or 4.

The apparatus of FIG. 5 is generally directed to this purpose. The apparatus, generally illustrated as 250, includes a dilution sample input 252 formed on a first analysis line 254 which connects the input 252 to a back pressure regulator 256. The output side of the regulator 254 is connected to an output line 258 which may be used to allow continuous delivery of the diluted gas for analysis by appropriate equipment provided at an analysis bench (not shown). A diluted sample pressure gauge 259 is fitted to the first analysis line 254.

Connected to the first analysis line 254 at a junction 260 is a second analysis line 262 which connects the line 254 to a mass flow controller 264 via the junction 260. The mass flow controller 264 receives the diluted sample (under pressure) and meters the gas allowed to pass therethrough in response to the predetermined control signals 266. Selective operation of the mass flow controller 264 is dictated by a measuring device 265 that outputs a control signal 266 to the controller 264 through a communication line 268 (shown in broken lines). A conduit 270 allows for distribution of the diluted sample to a plurality of sample collection bags 272, 274, 276, 278 through a like number of collection bag connecting lines 280, 282, 284, 286. A greater or lesser number of collection bags may be used. The bags 272, 274, 276, 278 are provided to allow the operator the option of collecting samples for later analysis. A series of solenoid valves 288, 290, 292, 294 are respectively fitted to the connecting lines 280, 282, 284, 286. The valves provide the operator with the ability to selectively close and open individual lines.

The line 254, the back pressure regulator 256, and the output line define an instantaneous analysis line, generally identified as 296. The second analysis line 262, the mass flow controller 264, the conduit 270, the collection bags 272, 274, 276, 278, and the lines 280, 282, 284, 286 define a bag collection line, generally identified as 298.

The analysis system 250 allows for continuous analysis of the diluted samples through operation of the instantaneous analysis line 288. The undiluted pollutant concentrations are first obtained by multiplying the diluted concentration by the dilution ratio. (As noted above, in practice, the dilution ratio is determined by analyzing the undiluted calibration gas and dividing that concentration by the concentration of the diluted calibration gas produced by the diluter as determined by the analyzer system.) The instantaneous exhaust concentration can then be multiplied by the corresponding exhaust mass flow rate to obtain the instantaneous mass flow rate of the pollutant. By integrating this mass flow rate over time, the total mass of pollutants produced during a test cycle can be obtained.

Alternately, by operation of the bag collection line 290, a sample of the diluted exhaust can be collected in the sample collection bags 272, 274, 276, 278 by metering a small amount of the diluted exhaust at a flow rate proportional to the exhaust flow rate using the mass flow controller 264 in response to control signals 266. Provided the control signals 266 are directly proportional to the exhaust gas flow rate, the total mass of pollutants can then be obtained by analysis of the sample collection bags 272, 274, 276, 278 and multiplying the concentration by the dilution ratio and the total exhaust volume. (The instantaneous exhaust flow rate and total exhaust volume can be determined by using existing techniques such as dilution air flow metering with the CVS.)

The arrangements of the present invention provide reliable, controllable, and accurate sample-diluent ratio control. In addition, the various diluter systems described above are effective within a wide range of exhaust pressures. Tests conducted have demonstrated that the exhaust pressure may be quickly varied from near-atmospheric to about 10 p.s.i.g., and back to atmospheric pressure with the dilution ratio being accurately maintained.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. An apparatus for controlling the dilution of an exhaust gas sample from the exhaust system of an engine for analysis, the apparatus comprising:

an exhaust gas sampling line through which passes a quantity of the exhaust gas sample, said exhaust gas sampling line having an orifice;

a source of substantially pollutant-free diluent gas;

a diluent line connected to said source of diluent gas, said diluent line having an orifice;

a diluent pressure regulator fitted to said diluent line and connected to said exhaust gas sampling line for controlling pressure such that said exhaust gas sampling line orifice and said diluent line orifice produce substantially equal pressure drops thereacross;

a diluent portion connected to said exhaust gas sampling line and said diluent line for diluting the exhaust gas sample with a quantity of said substantially pollutant-free diluent gas to create a diluted exhaust gas sample;

a delivery portion for delivering said diluted exhaust gas sample to an exhaust emission analyzer; and a system for directing said diluted exhaust gas sample to said exhaust emission analyzer at a flow rate sufficient for analysis.

2. The apparatus of claim 1, wherein said system includes a pressure regulator to allow continuous analyzing of said diluted exhaust gas sample.

3. The apparatus of claim 1, wherein said system includes at least one sample bag and means for metering the flow of said diluted exhaust gas sample to said at least one sample bag in proportion to the flow of said diluted exhaust gas sample.

4. The apparatus of claim 3, wherein said means for metering the flow to said at least one sample bag comprises a mass flow controller.

5. A method for preparing a diluted sample of exhaust gas from the exhaust system of an engine for analysis, said method including the steps of:

extracting an exhaust gas sample from the exhaust system of an engine and passing said exhaust gas sample through an exhaust gas sampling line having an orifice;

extracting a diluent gas from a diluent gas source and passing said diluent gas through a diluent line having an orifice;

fitting a pressure regulator to said diluent line and in connection with said exhaust gas sampling line;

controlling pressure such that said exhaust gas sampling line orifice produce substantially equal pressure drops thereacross, to maintain a substantially constant volumetric ratio of said exhaust gas sample and said diluent gas;

introducing said diluent gas into said exhaust gas sample to create a diluted exhaust gas sample;

establishing a dilution ratio between said diluent gas and said exhaust gas sample;

directing said diluted exhaust gas sample to an exhaust emission analyzer at a flow rate sufficient for analysis; and analyzing said diluted exhaust gas sample.

6. The method of claim 5, including the step of continuously analyzing said diluted exhaust gas sample.

7. The method of claim 5, including the step of collecting said diluted exhaust gas sample in at least one sample bag by metering said diluted exhaust gas sample at a flow rate proportional to the flow rate of said diluted exhaust gas sample using said metering device.

8. The method of claim 7, including the step of using a mass flow controller as said metering device.

9. The method of claim 7, further comprising the steps of:
   determining the total exhaust volume of said diluted exhaust gas sample;
   analyzing said at least one sample bag to obtain a total mass of any individual constituents in said diluted exhaust gas sample;
   obtaining a concentration for said individual constituents in said diluted exhaust gas sample; and
   multiplying said concentration of individual constituents in said diluted exhaust gas sample found in said sample bag by said dilution ratio and said total exhaust volume to obtain a total mass of said individual constituents in said diluted exhaust gas sample.

10. The method of claim 5, wherein said step of establishing a dilution ratio further comprises the following steps:
    introducing a calibration gas from a calibration gas source;
    passing said calibration gas through said diluent line;
    extracting a diluted calibration gas through said diluent line;
    maintaining the volumetric ratio of said diluted calibration gas and said calibration gas at a substantially constant rate;
    directing said diluted calibration gas to the exhaust emission analyzer to obtain a concentration for said calibration gas and a concentration for said diluted calibration gas; and
    dividing said concentration of said calibration gas by said concentration of said diluted calibration gas to determine said dilution ratio.

11. The method of claim 10, further comprising the steps of:
    obtaining individual diluted concentration rates for any individual constituents in said diluted exhaust gas sample;
    multiplying said diluted concentration rates of said individual constituents in said diluted exhaust gas sample by said dilution ratio to obtain an instantaneous exhaust concentration for said individual constituents; and
    multiplying said instantaneous exhaust concentration by an exhaust mass flow rate to obtain an instantaneous mass flow rate for said individual constituents in said diluted exhaust gas sample.

12. The method of claim 11, further comprising the step of:
    integrating said instantaneous mass flow rate over time, to obtain a total mass of pollutants produced.

13. An apparatus for controlling the dilution of an exhaust gas sample from the exhaust system of an engine for analysis, the apparatus comprising:
    an exhaust gas sampling line having first and second ends, said first end being fluidly connected to the exhaust system;
    an exhaust gas sampling line orifice fitted to said exhaust gas sampling line, said exhaust gas sampling line orifice having an inlet;
    a source of substantially pollutant-free diluent gas;
    a diluent line having first and second ends, said first end being connected to said source of substantially pollutant-free diluent gas;
    a diluent line orifice fitted to said diluent line, said diluent line orifice having an inlet;
    a diluent pressure regulator fitted to said diluent line and connected to said exhaust gas sampling line for controlling pressure such that said exhaust gas sampling line orifice and said diluent line orifice are configured so as to produce substantially equal pressure drops thereacross;
    a diluted gas outlet line having first and second ends, said first end being connected to an exhaust emission analyzer;
    a fluid junction, said second ends of said exhaust gas sampling line, said diluent line, and said diluted gas outlet line being connected to said fluid junction; and
    a system for drawing diluted exhaust gas sample through said diluted gas outlet line.

14. The apparatus of claim 13, wherein said system includes a pressure regulator to allow continuous analyzing of said diluted exhaust gas sample.

15. The apparatus of claim 13, wherein the exhaust emission analyzer includes at least one sample bag and means for metering the flow of said diluted exhaust gas sample to said at least one sample bag in proportion to the flow of said diluted exhaust gas sample.

16. The apparatus of claim 15, wherein said means for metering the flow to said at least one sample bag comprises a mass flow controller.

* * * * *